United States Patent
Skolnick

(10) Patent No.: US 11,471,437 B2
(45) Date of Patent: Oct. 18, 2022

(54) COMPOSITIONS AND METHODS FOR TREATING CANNABINOID HYPEREMESIS SYNDROME WITH A CANNABINOID RECEPTOR ANTAGONIST

(71) Applicant: Opiant Pharmaceuticals, Inc., Santa Monica, CA (US)

(72) Inventor: Phil Skolnick, Potomac, MD (US)

(73) Assignee: Opiant Pharmaceuticals, Inc., Santa Monica, CA (US)

( * ) Notice: Subject to any disclaimer, the term of this patent is extended or adjusted under 35 U.S.C. 154(b) by 166 days.

(21) Appl. No.: 16/904,359

(22) Filed: Jun. 17, 2020

(65) Prior Publication Data

US 2021/0015791 A1 Jan. 21, 2021

Related U.S. Application Data

(60) Provisional application No. 63/037,351, filed on Jun. 10, 2020, provisional application No. 62/862,830, filed on Jun. 18, 2019.

(51) Int. Cl.
*A61K 31/397* (2006.01)
*A61K 9/00* (2006.01)

(52) U.S. Cl.
CPC .......... *A61K 31/397* (2013.01); *A61K 9/0019* (2013.01)

(58) Field of Classification Search
CPC ........................... A61K 31/397; A61K 9/0019
See application file for complete search history.

(56) References Cited

U.S. PATENT DOCUMENTS

| | | | | |
|---|---|---|---|---|
| 6,355,631 | B1 * | 3/2002 | Achard | C07D 417/12 514/210.01 |
| 2007/0244085 | A1 | 10/2007 | Peracchia et al. | |
| 2008/0214559 | A1 | 9/2008 | Lange et al. | |
| 2009/0035219 | A1 | 2/2009 | Makriyannis et al. | |
| 2009/0311347 | A1 | 12/2009 | Oronsky et al. | |
| 2016/0008364 | A1 | 1/2016 | Alam | |
| 2018/0311205 | A1 | 11/2018 | Morgan | |
| 2020/0179271 | A1 | 6/2020 | Skolnick | |
| 2020/0397749 | A1 | 12/2020 | Skolnick | |

FOREIGN PATENT DOCUMENTS

| | | |
|---|---|---|
| WO | 2008024490 A2 | 2/2008 |
| WO | 2010/018856 A1 | 2/2010 |
| WO | 2013/068371 A1 | 5/2013 |
| WO | 2018/002636 A1 | 1/2018 |
| WO | 2018204689 A1 | 11/2018 |
| WO | 2020/118048 A1 | 6/2020 |
| WO | 2020/257333 A1 | 12/2020 |
| WO | 2020/257336 A1 | 12/2020 |

OTHER PUBLICATIONS

Zuurman et al., Inhibition of THC-Induced Effects on the Central Nervous System and Heart Rate by a Novel CB1 Receptor Antagonist AVE1625, 13 J. Psychopharm. 363-371 (2010) (Year: 2010).*
www.GenengNews.com Press Release (dated Oct. 27, 2018) (Year: 2018).*
Hoffman, A. et al., "Disruption of Hippocampal Synaptic Transmission and Long-Term Potentiation by Psychoactive Synthetic Cannabinoid 'Spice' Compounds: Comparison with Δ 9-Tetrahydrocannabinol", Addict Biol., 22(2):390-9, (2017).
International Application No. PCT/US2019/064672; International Search Report and Written Opinion of the International Searching Authority, dated Feb. 25, 2020; 8 pages.
Ishak, W. et al., Potential Cannabis Antagonists for Marijuana Intoxication, J Pharmacol Clin Toxicol (2018), 6(5): 1120, 9 pages.
Logan, B. et al., Reports of Adverse Events Associated with Use of Novel Psychoactive Substances, 2013-2016: A Review, Journal of Analytical Toxicology (2017), 41, 573-610.
Manseau, M. et al., Clinical Characteristics of Synthetic Cannabinoid Use in a Large Urban Psychiatric Emergency Setting, Substance Use & Misuse (2017), 52:6, 822-825.
Pryce, G. et al., "Antidote to Cannabinoid Intoxication: The CB1 Receptor Inverse Agonist, AM251, Reverses Hypothermic Effects of the CB1 Receptor Agonist, CB-13, in Mice", Br J Pharmacol., 174(21):3790-4, (2017).
Skolnick, P. et al., "Cannabinoid1 (CB-1) Receptor Antagonists: A Molecular Approach to Treating Acute Cannabinoid Overdose", J Neural Transm (Vienna), 127(2):279-86, (2020).
Black M.D et al.: "AVE1625, a cannabinoid CB1 receptor antagonist, as a co-treatment with antipsychotics for schizophrenia: improvement in cognitive function and reduction of antipsychotic-side effects in rodents", Psychopharmacology (Berl), 2011, vol. 215, No. 1, pp. 149-163, DOI: 10.1007/s00213-010-2124-0.
Galli et al. Cannabinoid Hyperemesis Syndrome. Curr Drug Abuse Rev. 2011:4(4):241-249). (Year: 2011).
Opiant, "Development Stage Specialty Pharma Company focused on Addiction and Drug Overdose", Mar. 2019 retrieved from https://ir.opiant.com/static-files/3b108da1-329b-486e-9ed7-e93b4146f8cd.
International Application No. PCT/US2020/038211; International Search Report and Written Opinion of the International Searching Authority, dated Nov. 3, 2020; 7 pages.
International Application No. PCT/US2020/038215; International Search Report and Written Opinion of the International Searching Authority, dated Oct. 20, 2020; 9 pages.
Crippa et al. (Harm Reduction Journal 2012;9(7):6 pages) (Year: 2012).

(Continued)

*Primary Examiner* — Timothy R Rozof
(74) *Attorney, Agent, or Firm* — Mayer Brown LLP

(57) ABSTRACT

Disclosed herein are formulations and methods for reversing one or more symptoms of cannabinoid hyperemesis syndrome (CHS) or one or more symptoms thereof, comprising parenterally administering a CB1 antagonist in an amount sufficient to reverse the CHS or symptom(s).

26 Claims, No Drawings

(56) References Cited

OTHER PUBLICATIONS

Vemuri et al. (Medicinal Chemistry of Cannabinoids. Clinical Pharmacology & Therapeutics 2015;97(6):553-558). (Year: 2015).
Richards J. R., et al., "Pharmacologic Treatment of Cannabinoid Hyperemesis Syndrome: A Systematic Review," Pharmacotherapy 2017;37(6):725-734.

* cited by examiner

COMPOSITIONS AND METHODS FOR TREATING CANNABINOID HYPEREMESIS SYNDROME WITH A CANNABINOID RECEPTOR ANTAGONIST

This application claims the benefit of priority of U.S. Provisional Application No. 62/862,830, filed Jun. 18, 2019, and U.S. Provisional Application No. 63/037,351, filed Jun. 10, 2020, the disclosures of which are hereby incorporated by reference as if written herein in their entireties.

Cannabinoid use can produce a syndrome which includes incapacitating, cyclic bouts of nausea and vomiting. The severe nausea and vomiting that is associated with chronic cannabinoid use is commonly referred to as cannabinoid hyperemesis syndrome (CHS). CHS can be viewed as paradoxical, since a synthetic form of $\Delta^9$-tetrahydrocannabinol (THC), the principal psychoactive compound present in cannabis, has been approved by the U.S. FDA (and regulatory authorities in other countries) for the treatment of chemotherapy-induced nausea and vomiting.

Patients with CHS present to the emergency department (ED) with periodic episodes of intractable vomiting that are generally unresponsive to standard antiemetics such as ondansetron and promethazine. These patients can first exhibit severe anxiety and agitation, flushing, and sweating. Patients frequently also experience abdominal pain and severe nausea that can be triggered by the sight or smell of food. These symptoms are followed by a second phase consisting of severe, often incapacitating nausea and vomiting. During this period, patients often take very hot baths to relieve these symptoms; this can result in burns from immersion in scalding water. Resolution of nausea and vomiting may require 24-48 hours, during which time patients receive fluids and electrolyte replacement. Complete cessation of cannabinoid use during this period is critical for symptom relief. However, the interval from cessation of cannabis use to complete resolution of symptoms (e.g. abdominal pain) may be as along as 1-4 weeks. Patients treated for CHS in the emergency department often require admission to better manage both the emesis and the ensuing dehydration, electrolyte imbalance, and esophagitis that result from the frequent and severe vomiting.

Authorities consider CHS distinct from acute cannabinoid overdose (also known as acute cannabinoid poisoning or intoxication) because of distinct symptoms and temporal patterning.

Although the molecular mechanisms responsible for CHS have not been precisely defined, both the links to cannabinoid use as a trigger and the cessation of use to symptom relief strongly suggest that cannabinoid receptors, proteins that mediate the pharmacological effects of THC, are responsible for mediating the primary symptoms (e.g., abdominal pain, cyclic nausea and vomiting episodes) characteristic of CHS. The well-described antiemetic effects of THC make the symptoms of CHS, especially the severe and cyclic vomiting, appear paradoxical, because cannabinoid receptors (specifically the CB-1 subtype) within brain centers known to control vomiting mediate these antiemetic effects of THC. However, long term, frequent cannabinoid consumption that is claimed to be a requisite for the emergence of CHS, may also sensitize CB-1 receptors located on the nerves within the gastrointestinal tract resulting in the characteristic stomach pain, cyclic nausea and vomiting of CHS.

CHS does not respond to standard antiemetics, and there are no medications with demonstrated efficacy in treating the symptoms (i.e., abdominal pain, nausea, and vomiting) of CHS which trigger emergency department visits and subsequent hospital admissions. Patients generally receive intravenous fluids and electrolytes, and are instructed to stop using cannabinoids. Thus, there is a clear need for rapid acting, specific medications to reverse the symptoms of CHS.

The identification of cannabinoid receptors more than 25 years ago led to the synthesis of many compounds which bind to these receptors with high affinity and specificity. Moreover, compounds have been identified that, on binding to cannabinoid receptors, and specifically the CB-1 receptor subtype, function as antagonists. That is, unlike THC and other cannabinoids which mimic the effects of THC (act as agonists), these compounds do not activate CB-1 receptor mediated signaling but can block or reverse the pharmacological effects of cannabinoids mediated via these receptors. Multiple, structurally diverse high affinity CB-1 antagonists have been described in the peer reviewed literature. Consistent with this body of literature, there are two clinical studies demonstrating that oral administration of CB-1 antagonists (surinabant, drinabant) can prevent (that is, block) some of the pharmacological effects of smoked or inhaled THC in normal volunteers. However, the slow onset of these compounds following oral administration (maximum plasma concentrations achieved in 2-3 h) and the core symptoms of CHS (abdominal pain, nausea, and vomiting) make oral dosing impractical. In order to be useful and effective in treating CHS, a CB-1 antagonist must be able to produce a clinically meaningful reduction in the core symptoms of CHS and be administered by a route that insures rapid onset and full delivery of the desired dose.

Accordingly, described herein are compositions and methods for alleviating the symptoms of cannabinoid hyperemesis syndrome (CHS) using the CB-1 antagonist drinabant (AVE 1625) or a salt or polymorph thereof via parenteral administration.

DETAILED DESCRIPTION

Disclosed herein are compositions and methods to treat, reverse, or reduce cannabinoid hyperemesis syndrome (CHS) or one or more symptoms thereof comprising parenterally administering a CB1 antagonist in an amount sufficient to reverse the symptom(s).

In certain embodiments, the CB-1 antagonist is drinabant, or a salt or polymorph thereof.

In certain embodiments, the plasma concentration of drinabant sufficient to reverse the cannabinoid overdose symptom(s) ranges from about 200 to about 730 ng/ml.

In certain embodiments, such as, for example, in an emergency setting, the parenteral route of administration is chosen from among intravenous (IV), intramuscular (IM), and subcutaneous (SC).

In certain embodiments, the amount of drinabant, or a salt or polymorph thereof. sufficient to reverse the CHS symptom(s) is between about 1 mg and about 150 mg per dose, between about 1 mg and about 100 mg per dose, between about 1 mg and about 60 mg per dose, between about 15 mg and about 60 mg per dose, between about 30 mg and about 60 mg per dose, between about 15 mg and about 30 mg per dose.

In certain embodiments, the parenteral route of administration is IV.

In certain embodiments, the amount of drinabant, or a salt or polymorph thereof. sufficient to reverse the CHS symptom(s) is between about 1 mg and about 60 mg per IV dose.

In certain embodiments, the amount of drinabant, or a salt or polymorph thereof, sufficient to reverse the CHS symptom(s) is between about 15 mg and about 60 mg per IV dose.

In certain embodiments, the amount of drinabant, or a salt or polymorph thereof, sufficient to reverse the CHS symptom(s) is between about 15 mg and about 30 mg per IV dose.

In certain embodiments, the amount of drinabant, or a salt or polymorph thereof, sufficient to reverse the CHS symptom(s) is between about 30 mg and about 60 mg per IV dose.

In certain embodiments, the IV dose is delivered by IV injection.

In certain embodiments, the IV dose is delivered in a liquid volume of between about 1 and about 20 mL.

In certain embodiments, the IV dose is delivered in a liquid volume of between about 1 and about 20 mL, distributed across two or more pushes.

In certain embodiments, the IV dose is delivered by IV infusion (IVN).

In certain embodiments, the IVN dose is delivered in a liquid volume of about 50 mL to about 500 mL, about 50 mL to about 125 mL, or about 250 mL to about 500 mL. In certain embodiments, the IVN dose is delivered in a liquid volume of about 50 mL, about 100 mL, about 125 mL, about 250 mL, or about 500 mL.

In certain embodiments, the IVN dose is delivered over a period of about 30 min to about 120 min. In certain embodiments, the IVN dose is delivered over a period of about 30 min, about 60 min, about 90 min, or about 120 min.

In certain embodiments, the IVN dose is delivered in a liquid volume of between about 125 to about 500 mL.

In certain embodiments, the IVN dose is delivered over a period of about 1 hour to about 2 hours.

In certain embodiments, the IVN dose is delivered at a rate of about 0.5 mL/min to about 2 mL/min.

In certain embodiments, the parenteral route of administration is IM or SC.

In certain embodiments, the amount of drinabant, or a salt or polymorph thereof sufficient to reverse the cannabinoid overdose symptom(s) is between about 5 mg and about 100 mg per IM dose.

In certain embodiments, the amount of drinabant, or a salt or polymorph thereof sufficient to treat, reverse, or reduce the CHS or one or more symptoms thereof is between about 5 mg and about 60 mg per IM dose.

In certain embodiments, the amount of drinabant, or a salt or polymorph thereof sufficient to treat, reverse, or reduce the CHS or one or more symptoms thereof is between about 15 mg and about 60 mg per IM dose.

In certain embodiments, the amount of drinabant, or a salt or polymorph thereof sufficient to treat, reverse, or reduce the CHS or one or more symptoms thereof is between about 15 mg and about 30 mg per IM dose.

In certain embodiments, the amount of drinabant, or a salt or polymorph thereof sufficient to treat, reverse, or reduce the CHS or one or more symptoms thereof is between about 30 mg and about 60 mg per IM dose.

In certain embodiments, the IM dose is delivered in a liquid volume of up to about 2.5 ml. In certain embodiments, the IM dose is delivered in a liquid volume of about 1 mL to about 2.5 ml.

In certain embodiments, the IM dose is delivered by injection into a deltoid or gluteal muscle.

In certain embodiments, the amount of drinabant, or a salt or polymorph thereof sufficient to treat, reverse, or reduce the CHS or one or more symptoms thereof is between about 1 mg and about 100 mg per SC dose.

In certain embodiments, the amount of drinabant, or a salt or polymorph thereof sufficient to treat, reverse, or reduce the CHS or one or more symptoms thereof is between about 5 mg and about 100 mg per SC dose.

In certain embodiments, the amount of drinabant, or a salt or polymorph thereof sufficient to treat, reverse, or reduce the CHS or one or more symptoms thereof is between about 5 mg and about 60 mg per IM dose.

In certain embodiments, the amount of drinabant, or a salt or polymorph thereof sufficient to treat, reverse, or reduce the CHS or one or more symptoms thereof is between about 15 mg and about 60 mg per IM dose.

In certain embodiments, the amount of drinabant, or a salt or polymorph thereof sufficient to treat, reverse, or reduce the CHS or one or more symptoms thereof is between about 15 mg and about 30 mg per IM dose.

In certain embodiments, the amount of drinabant, or a salt or polymorph thereof sufficient to treat, reverse, or reduce the CHS or one or more symptoms thereof is between about 30 mg and about 60 mg per IM dose.

In certain embodiments, the SC dose is delivered in a liquid volume of up to about 1.5 ml. In certain embodiments, the SC dose is delivered in a liquid volume of about 1 mL to about 1.5 ml.

In certain embodiments, the IV, IVN, IM, or SC dose or injection is delivered as a solution, suspension or emulsion.

In certain embodiments, the IV, IVN, IM, or SC dose or injection contains at least one agent that acts as a non-ionic solubilizer and/or emulsifying agent.

In certain embodiments, the agent that acts as a non-ionic solubilizer and/or emulsifying agent comprises polyoxyl 15 hydroxystearate or a mixture of polyglycol mono- and di-esters of 12-hydroxystearic acid.

In certain embodiments, the agent that acts as a non-ionic solubilizer and/or emulsifying agent which comprises polyoxyl 15 hydroxystearate is Kolliphor® HS 15 (CAS No. 70142-34-6) or Solutol HS 15 (polyglycol mono- and di-esters of 12-hydroxystearic acid with about 30% polyethylene glycol).

In certain embodiments, the symptom(s) of CHS are chosen from abdominal pain, nausea, and vomiting.

In certain embodiments, the onset of reversal of symptom(s) of CHS are apparent within 5-30 minutes following IV injection of drinabant, or a salt or polymorph thereof.

In certain embodiments, the onset of reversal of symptom(s) of cannabinoid overdose are apparent within 30-60 minutes following IVN injection of drinabant, or a salt or polymorph thereof.

In certain embodiments, the onset of reversal of symptom(s) of CHS are apparent within about 15 min to about 45 min following IM or SC administration of drinabant, or a salt or polymorph thereof.

In certain embodiments, if no response is observed within about 30 minutes to about two hours of a first administration of drinabant, and the presence of cannabinoids is confirmed or strongly suspected, a second dose may be administered.

Definitions

As used herein, reversal, attenuation or reduction of CHS symptom(s) is apparent when, in the judgment of a trained healthcare giver (e.g., physician, nurse practitioner, nurse, paramedic, or emergency medical technician), the symptom(s) have abated to a noticeable degree, which is interpreted as a clinically meaningful reduction in the frequency or severity of symptoms. Such a caregiver may use any appropriate measure to quantify the reversal of symptom(s), e.g., the number of bouts of vomiting and/or nausea, number of patient complaints of abdominal pain or discomfort etc. Similarly, visual analog scales (VAS) can be used to quantify a reduction in severity (e.g. rate the abdominal pain on a scale from 1 to 10 with 1 as little or no discomfort to 10 as "worst pain ever")—such scales can also be used by the patient to assess the severity of nausea and vomiting bouts. The "apparent" reversal or attenuation of symptom(s) includes, but need not extend to, complete cessation of symptoms.

As used herein, the term "cannabinoid" is synonymous with "cannabinoid receptor agonist" and refers to a compound or compounds which binds to and activates a cannabinoid receptor. This would include cannabinoids and structurally related compounds found in cannabis, but also term includes synthetic compounds that are structurally unrelated to THC and other chemicals found in cannabis.

As used herein, the term "cannabinoid receptor antagonist" refers to a compound which binds to and blocks or dampens the normal biological function of the receptor and its signaling, especially in the presence of an agonist or partial agonist. The term includes cannabinoid receptor antagonists that are selective or nonselective for the CB1 receptor subtype, i.e., a "CB1 antagonist."

As used herein, the term "intramuscular (IM)" means administered into a muscle. Suitable muscles, if of sufficient mass, include the deltoid (upper arm), the thigh (esp. the anterolateral aspect of the thigh; particularly useful if via an autoinjector), the gluteus maximus (typically only adults and children >3 years old), and hip. The IM injection may be via a classical syringe or an autoinjector device.

As used herein, the term "intravenous (IV)" means delivered as a liquid into a vein of a patient. Intravenous administration can be by injection (in a relatively small volume and at relatively high concentration) by injection via a syringe or into a previously-inserted IV catheter, or by intravenous infusion ("IVN," in a relatively larger and more dilute volume). IV administration, particularly injection, can be done in one or more pushes.

The terms "non-ionic solubilizer" and/or "emulsifying agent" and/or "solubilizing agent" are generally interchangeable as used herein, and include agents that result in formation of a micellar solution or a true solution of the agent being solubilized and a typically immiscible partner (for example, drinabant, which has a high log P, and water, which has a negative log P). Solubilizing agents include cationic and nonionic surfactants, and in certain circumstances may also act as absorption or permeation enhancers. One example of a solubilizing agent is Kolliphor HS 15/Solutol HS 15 (e.g., CAS No. 70142-34-6 or 61909-81-7, polyoxyl 15 hydroxystearate, polyglycol mono- and di-esters of 12-hydroxystearic acid with about 30% polyethylene glycol).

As used herein, the term "parenteral" means administered by means other than oral, nasal (i.e., bypassing mucous membranes) or rectal intake, particularly intravenously or by injection elsewhere, e.g., intramuscular or subcutaneous injection.

As used herein, the term "push" in the context of an intravenous (IV) push is the rapid administration of a small volume of medication into a patient's vein, typically via a previously inserted IV catheter. Multiple pushes make be used to comprise a single IV dose.

As used herein, the term "subcutaneous" means "under the skin," i.e., administered into the subcutis, the layer of skin directly below the dermis and epidermis (collectively referred to as the cutis), above muscle.

As used herein, a "symptom" of CHS is a physical or mental feature that is regarded as is a departure from normal function or feeling. Typical features of CHS are well known to those skilled in the art and are described in the literature, generally including severe, cyclic nausea and vomiting that is not relieved by standard anti-nausea agents (e.g. ondansetron), and abdominal pain (that can be generalized or more local (e.g., epigastric or periumbilical).

As used herein, the term "in need of treatment" and the term "in need thereof" when referring to treatment are used interchangeably and refer to a judgment made by a health caregiver (e.g. physician, nurse, nurse practitioner, that a patient will benefit from treatment.

As used herein, the term "subject" is intended to be synonymous with "patient," and refers to any mammal (preferably human) who exhibits symptoms associated with CHS described herein and falls into a 'high risk' category (individuals with a history of long term, frequent cannabis: 68% of patients consumed cannabis for >2 years before symptoms occurred; 95% used cannabis more than once a week.

As used herein, to "treat," "treating," "treatment," and the like in reference to CHS means, to a clinically meaningful degree, to reduce, attenuate, reverse, or eliminate its cause or progression, or the severity and/or frequency of one or more of its symptoms, or otherwise ameliorate CHS in a subject.

Cannabinoid Receptor Antagonists

Cannabinoid receptor antagonists are known in the art, and may be selective or nonselective for CB1. Potency and selectivity for the CB1 receptor are generally desirable because cannabinoids producing CHS are CB1 agonists. Rimonabant (5-(4-chlorophenyl)-1-(2,4-dichloro-phenyl)-4-methyl-N-(piperidin-1-yl)-1H-pyrazole-3-carboxamide) was the first-developed potent and selective CB1 antagonist, once approved as an anti-obesity agent in Europe. Many CB1 antagonists reported so far are 1,5-diarylpyrazole analogs, often featuring a para-substituted phenyl ring at the pyrazole 5-position and a 2,4-dichloro-substituted phenyl ring at the pyrazole 1-position. Other analogues in this class include surinabant and AM-251. Additional analogues featuring core replacements include 3,4-diarylpyrazolines, 4,5-diarylimidazoles, and 1,5-diarylpyrrole-3-carboxamides, fused bicyclic derivatives of diaryl-pyrazole, diaryl-imidazole, diaryl-purines (e.g. otenabant), six-membered ring pyrazole bioisosteres such as 2,3-diarylpyridines and 2,3-diarylpyrimidines, and methylsulfonamide azetidine derivatives. This last class includes drinabant ((±)-N-{1-[bis(4-chlorophenyl)methyl]-3-azetidinyl}-N-(3,5-difluorophenyl) methanesulfonamide), also potent and selective for CB1. Rimonabant, once approved as an oral formulation for the treatment of obesity and smoking cessation in Europe, was withdrawn from the European market, and the development of drinabant halted, due to rimonabant's concerning side effects including psychiatric effects such as depression and mood alterations.

However, these side effects are of far less concern when the intended use, instead of daily and long-term, will be limited to indications where the administration is acute and transient, such as reversal the symptoms of CHS. Accordingly, any potent and selective CB1 antagonist with adequate target tissue penetration would be expected to work in the methods and formulations disclosed herein.

Plasma concentrations of CB1 antagonists useful in reversing the symptoms of CHS will vary based on several factors, including the identity of the antagonist. For example, plasma concentrations of drinanbant useful in reversing the symptoms of cannabinoid overdose range from about 200 ng/mL to about 730 ng/mL. Additionally, it is understood by those skilled in the art that the because drinabant has been characterized as a competitive CB1 receptor antagonist, effective (therapeutic) plasma concentrations are dependent upon the dose and type of cannabinoid responsible, and the frequency and duration the cannabinoid has been taken. Both the onset and degree of symptom relief may vary, and some symptoms (e.g. abdominal pain) may be more sensitive to reversal than others (e.g., nausea). It is anticipated that onset of symptom relief should be apparent within about 5 min to about 30 min following intravenous administration and about 15 min to about 45 min following intramuscular or subcutaneous administration, respectively.

In order to achieve these plasma concentrations, intravenous doses of drinabant of between about 1 mg and about 150 mg, about 1 mg and about 100 mg, or between about 1 mg and about 60 mg, or between about 15 mg and about 60 mg, or between about 30 mg and about 60 mg, or between about 1 mg and about 30 mg, or between about 15 mg and about 30 mg, or between about 50 mg and about 100 mg may be administered. Intravenous doses can be injected in volumes of about 1 to about 20 mL (lower volumes are preferred in certain circumstances).

Alternatively, in order to achieve these plasma concentrations, intramuscular or subcutaneous doses of drinabant of between about 1 mg and about 150 mg, about 5 mg and about 100 mg, or between about 5 mg and about 60 mg, or between about 15 mg and about 60 mg, or between about 30 mg and about 60 mg, or between about 15 mg and about 30 mg, or between about 50 mg and about 100 mg, or between about 5 mg and about 50 mg, or between about 5 mg and about 30 mg. Intramuscular or subcutaneous doses can be injected in a volume of up to about 2.5 mL for IM and about 1.5 mL for SC. Intramuscular injections are typically into a deltoid or gluteal muscle.

In certain embodiments, the doses above take into account the possibility that fatty tissue may act as a sink for a lipophilic cannabinoid antagonist, which may diffuse in and out of the fatty tissue over time. In any event, if no response is observed with ~30-45 minutes of parenteral administration, and the presence of cannabinoids is confirmed or strongly suspected, a second dose may be administered.

Examples

Table 1 below discloses several examples of compositions which can be formulated for parenteral administration (i.e., as liquid preparations) comprising an amount of drinabant or a salt or polymorph thereof effective to reverse CHS or one or more symptoms thereof in a subject.

TABLE 1

| Ex. | Mode | Dose, mg | Vol, mL |
|---|---|---|---|
| 1 | IV | 1 | 1 |
| 2 | IV | 1 | 2 |
| 3 | IV | 1 | 3 |
| 4 | IV | 1 | 5 |
| 5 | IV | 1 | 10 |
| 6 | IV | 5 | 1 |
| 7 | IV | 5 | 2 |
| 8 | IV | 5 | 3 |
| 9 | IV | 5 | 5 |
| 10 | IV | 5 | 10 |
| 11 | IV | 15 | 1 |
| 12 | IV | 15 | 2 |
| 13 | IV | 15 | 3 |
| 14 | IV | 15 | 5 |
| 15 | IV | 15 | 10 |
| 16 | IV | 30 | 1 |
| 17 | IV | 30 | 2 |
| 18 | IV | 30 | 3 |
| 19 | IV | 30 | 5 |
| 20 | IV | 30 | 10 |
| 21 | IV | 45 | 1 |
| 22 | IV | 45 | 2 |
| 23 | IV | 45 | 3 |
| 24 | IV | 45 | 5 |
| 25 | IV | 45 | 10 |
| 26 | IV | 60 | 1 |
| 27 | IV | 60 | 2 |
| 28 | IV | 60 | 3 |
| 29 | IV | 60 | 5 |
| 30 | IV | 60 | 10 |
| 31 | IV | 100 | 1 |
| 32 | IV | 100 | 2 |
| 33 | IV | 100 | 3 |
| 34 | IV | 100 | 5 |
| 35 | IV | 100 | 10 |
| 36 | IM | 5 | 1 |
| 37 | IM | 5 | 1.5 |
| 38 | IM | 5 | 2 |
| 39 | IM | 5 | 2.5 |
| 40 | IM | 15 | 1 |
| 41 | IM | 15 | 1.5 |
| 42 | IM | 15 | 2 |
| 43 | IM | 15 | 2.5 |
| 44 | IM | 30 | 1 |
| 45 | IM | 30 | 1.5 |
| 46 | IM | 30 | 2 |
| 47 | IM | 30 | 2.5 |
| 48 | IM | 45 | 1 |
| 49 | IM | 45 | 1.5 |
| 50 | IM | 45 | 2 |
| 51 | IM | 45 | 2.5 |
| 52 | IM | 60 | 1 |
| 53 | IM | 60 | 1.5 |
| 54 | IM | 60 | 2 |
| 55 | IM | 60 | 2.5 |
| 56 | IM | 100 | 1 |
| 57 | IM | 100 | 1.5 |
| 58 | IM | 100 | 2 |
| 59 | IM | 100 | 2.5 |
| 60 | SC | 5 | 0.5 |
| 61 | SC | 5 | 1 |
| 62 | SC | 5 | 1.5 |
| 63 | SC | 15 | 0.5 |
| 64 | SC | 15 | 1 |
| 65 | SC | 15 | 1.5 |
| 66 | SC | 30 | 0.5 |
| 67 | SC | 30 | 1 |
| 68 | SC | 30 | 1.5 |
| 69 | SC | 45 | 0.5 |
| 70 | SC | 45 | 1 |
| 71 | SC | 45 | 1.5 |
| 72 | SC | 60 | 0.5 |
| 73 | SC | 60 | 1 |
| 74 | SC | 60 | 1.5 |
| 75 | SC | 100 | 0.5 |
| 76 | SC | 100 | 1 |
| 77 | SC | 100 | 1.5 |

Table 2 below discloses several examples of compositions which can be formulated for parenteral administration as an IV infusion, comprising an amount of drinabant or a salt or polymorph thereof effective to reverse the cannabinoid overdose or one or more symptoms thereof in a subject. The drinabant may be delivered, e.g., over the given time interval (period, in minutes) below.

TABLE 2

| Ex. | Mode | Dose, mg | Vol., mL | Per., min |
|---|---|---|---|---|
| 78 | IVN | 5 | 50 | 30 |
| 79 | IVN | 5 | 100 | 30 |
| 80 | IVN | 5 | 125 | 30 |
| 81 | IVN | 15 | 50 | 30 |
| 82 | IVN | 15 | 100 | 30 |
| 83 | IVN | 15 | 125 | 30 |
| 84 | IVN | 30 | 125 | 60 |
| 85 | IVN | 30 | 125 | 90 |
| 86 | IVN | 30 | 125 | 120 |
| 87 | IVN | 30 | 250 | 60 |
| 88 | IVN | 30 | 250 | 90 |
| 89 | IVN | 30 | 250 | 120 |
| 90 | IVN | 45 | 250 | 60 |
| 91 | IVN | 45 | 250 | 90 |
| 92 | IVN | 45 | 250 | 120 |
| 93 | IVN | 45 | 500 | 60 |
| 94 | IVN | 45 | 500 | 90 |
| 95 | IVN | 45 | 500 | 120 |
| 96 | IVN | 60 | 250 | 60 |
| 97 | IVN | 60 | 250 | 90 |
| 98 | IVN | 60 | 250 | 120 |
| 99 | IVN | 60 | 500 | 60 |
| 100 | IVN | 60 | 500 | 90 |
| 101 | IVN | 60 | 500 | 120 |

Assays and Protocols

Clinical Trial Protocol for CHS

The efficacy of cannabinoid antagonists e.g. drinabant may be tested in a field trial, e.g. of patients presenting at a health care facility such as an emergency department (ED).

Inclusion and enrollment. In the following proposed double-blind, placebo-controlled field trial protocol, a subject would qualify for inclusion if, in the ED physician's opinion, the individual fulfills both the specified symptom set and profile of a CHS patient, and receives a diagnosis of CHS. Such symptoms and profile features of CHS include, e.g., the following:
1. chronic, heavy use of cannabinoids such as smoked cannabis;
2. cyclic/recurrent episodes of severe nausea and intractable vomiting; and, optionally:
3. abdominal pain;
4. prior experience of temporary relief of symptoms by taking a hot bath or shower; and
5. prior experience of resolution of symptoms when cannabis use is stopped.

Additional symptoms and patient profile characteristics mat be deemed relevant; see, e.g., Sorensen C J et al., "Cannabinoid Hyperemesis Syndrome: Diagnosis, Pathophysiology, and Treatment—a Systematic Review," *J Med Toxicol* 2017, 13(1): 71-87; Sullivan S., "Cannabinoid hyperemesis," *Can J Gastroenterol* 2010, 24(5): 284-85. If in the physician's judgment inclusion criteria are met, and in the physician's judgment no criteria present a safety risk sufficient to exclude the subject, and the subject gives informed consent, the subject may enter the trial.

Baseline Assessments. Prior to intervention, baseline assessments are taken of the following symptoms in each patient and recorded:
frequency of bouts of nausea;
severity of nausea (using a visual analog scale (VAS));
frequency of vomiting;
severity of vomiting (using a VAS);
frequency of abdominal pain; and
severity of abdominal pain (using a VAS).

Optionally, other symptoms may be followed (e.g. esophagitis, which is secondary to vomiting and more difficult to quantify), but these comprise the "core" symptoms of CHS as presently understood. See, e.g., Simonetto D A et al., "Cannabinoid hyperemesis: a case series of 98 patients," Mayo Clin Proc. 2012 February; 87(2):114-9. Assessments may be self-reported or observed by the clinician and these should be distinguished.

Visual analog scales are known in the art. For example, a visual analog scale for nausea is disclosed in Meek R et al., "Use of the visual analog scale to rate and monitor severity of nausea in the emergency department," *Acad Emerg Med* 2009, 16(12):1304-1310. In this study, a "standard 100 mm" VAS (from no nausea to nausea as bad as it possibly could be) was used alongside self-reporting of nausea in emergency department patients reporting nausea on a Likert scale as "none, mild, moderate, or severe" at enrollment, 30 minutes, and 60 minutes, and patients were also "asked to describe any change in nausea severity from the previous rating (a lot less, a little less, the same, a little more, or a lot more)." The study found "very good correlation between verbal descriptors of nausea and VAS ratings," and the "minimum clinically significant difference (MCSD) in VAS rating of nausea severity" was determined to be 22 mm. Other studies of nausea and vomiting reporting and VAS use somewhat different VAS scales (such as 0 to 5 or 0 to 10) and/or assess frequency of vomiting/dry retching (none, sometimes, most of the time, all the time; none, once or twice, three times or more in the last given unit of time; fraction of the last hour or other unit of time), and/or assess the persistence of the nausea (constant or intermittent). It is within the skill of the clinician to select the criteria most informative for efficacy readout in the trial.

These assessments will be repeated following interventions as discussed below.

Randomization and Intervention. Subjects are randomized according to the following protocol to receive, in addition to symptomatic treatment (fluids and/or electrolytes), either:
IV drinabant administered at one or more doses sufficient to achieve a plasma concentration in the range of from about 200 ng/mL to about 730 ng/mL, in about 1 to about 20 mL (lower preferred)—for example, between about 1 and about 60 mg (by way of more specific example, between about 15 and about 60 mg, or between about 30 and about 60 mg);
or placebo, in a similar volume.

Alternatively or in addition—either concurrently or after reversal is achieved via the IV route—IM- and/or SC-dosed groups may be employed or similar trials constructed, with dosing as set forth in paragraphs above in a volume of about up to about 2.5 mL for IM doses and/or in a volume of about up to about 1.5 mL for SC doses.

The intervention is administered (placebo or active) and the subject is then observed for, e.g., 2 hours. During this time, the physician re-assesses symptoms as disclosed above; this may be done multiple times. If after dosing, in the opinion of the physician, there is no diminution in symptoms within 2 hours, the subject is administered a dose of second dose of this treatment (either placebo or active) via the same route as the first dose, and is observed for another 2 hours. Again, during this time, the physician re-assesses symptoms as disclosed above; this may be done multiple times. If symptoms have not improved within this further 2 hours, the subject receives a third administration consisting of the other treatment, via the same route as the first two doses. For example, if the subject receives 2 doses of active via the IV route and there is no improvement, the subject would receive placebo via the IV route, and visa-versa. In this way, patients would receive no more than 2 doses of active. At least one final assessment is done as disclosed above.

Results. An intervention with an active pharmaceutical ingredient, e.g., drinabant, is deemed effective if it reduces compared to placebo the frequency and/or severity of i) nausea, ii) bouts of vomiting, and/or iii) abdominal pain in a clinically meaningful fashion compared to placebo. In CHS, a response rate twice that of placebo would be considered a clinically meaningful improvement to those skilled in the art. For example, if 30% of placebo-treated patients show a clinically meaningful improvement in one or more of the trial measures described above, drinabant administration would result in an improvement in at least 60% the patients. This would result in a 'number needed to treat' (NNT), a statistical measure commonly used to assess drug efficacy, of 3.3 (1/0.6-0.3), a value that would encourage use of this medication by ED physicians. It is expected that drinabant, administered at a dose sufficient to achieve a plasma concentration in the range of from about 200 ng/mL to about 730 ng/mL, will reduce compared to placebo the frequency and/or severity of i) nausea, ii) bouts of vomiting, and/or iii) abdominal pain in a clinically meaningful fashion.

Solubility Protocol

Drinabant may be added to a fixed volume of aqueous solution with and without various amounts of water soluble carriers such as Solutol HS 15 in screw capped bottles. Samples are shaken (alternatively, stirred) for a length of time (e.g., 48 hours) at room temperature, pH optionally adjusted, and any suspensions filtered through, e.g., a Whatman filter paper no 1. Filtered solutions are then analyzed for drinabant concentration using an appropriate method such as UV/visible spectrophotometry at an appropriate wavelength (nm) or by HPLC. It is expected that at low concentrations of solubilizing agent (e.g., 1, 5, or 10%), improvement in solubility will increase linearly, but that at higher concentrations this trend may deviate.

Although the present invention has been described with reference to specific details of certain embodiments thereof in the above examples, it will be understood that modifications and variations are encompassed within the spirit and scope of the invention.

What is claimed is:

1. A composition formulated for parenteral administration comprising an amount of drinabant, or a salt or polymorph thereof, effective to treat, reverse, or reduce cannabinoid hyperemesis syndrome (CHS) or one or more symptoms thereof in a subject.

2. A method of treating, reversing, or reducing CHS or one or more symptoms thereof in a subject comprising parenterally administering to the subject an amount of drinabant or a salt or polymorph thereof, effective to treat, reverse, or reduce cannabinoid hyperemesis syndrome (CHS) or one or more symptoms thereof.

3. The method as recited in claim 2, wherein the plasma concentrations achieved by parenteral administration of drinabant or salt or polymorph thereof sufficient to treat, reverse, or reduce the CHS or one or more symptoms thereof is 200 to about 730 ng/ml.

4. The method as recited in claim 3, wherein the parenteral route of administration is chosen from among intravenous (IV), intramuscular (IM), and subcutaneous (SC).

5. The method as recited in claim 4, wherein the parenteral route of administration is IV.

6. The method as recited in claim 5, wherein the amount of drinabant, or a salt or polymorph thereof, sufficient to treat, reverse, or reduce the CHS or one or more symptoms thereof is between about 1 mg and about 100 mg per intravenous dose.

7. The method as recited in claim 6, wherein the amount of drinabant, or a salt or polymorph thereof sufficient to treat, reverse, or reduce the CHS or one or more symptoms thereof is between about 30 and about 100 mg per intravenous dose.

8. The method as recited in claim 5, wherein the IV dose is delivered by IV injection.

9. The method as recited in claim 8, wherein the IV dose is delivered in a liquid volume of between about 1 and about 20 mL.

10. The method as recited in claim 5, wherein the IV dose is delivered by IV infusion.

11. The method as recited in claim 10, wherein the IV infusion is delivered in a liquid volume of between about 50 to about 500 mL.

12. The method as recited in claim 11, wherein the IV infusion is delivered over a period of about 30 min to about 2 hours.

13. The method as recited in claim 11, wherein the IV infusion is delivered at a rate of about 0.5 mL/min to about 2 mL/min.

14. The method as recited in claim 4, wherein the parenteral route of administration is IM or SC.

15. The method as recited in claim 14, wherein the amount of drinabant, or a salt or polymorph thereof sufficient to treat, reverse, or reduce the CHS or one or more symptoms thereof is between about 5 and about 60 mg per IM or SC dose.

16. The method as recited in claim 15, wherein the amount of drinabant, or a salt or polymorph thereof sufficient to treat, reverse, or reduce the CHS or one or more symptoms thereof is between about 5 and about 30 mg per IM or SC dose.

17. The method as recited in claim 15, wherein the intramuscular dose is delivered in a liquid volume of up to about 2.5 mL.

18. The method as recited in claim 17, wherein the intramuscular dose is delivered in a liquid volume of about 1 to about 2.5 mL.

19. The method as recited in claim 15, wherein the SC dose is delivered in a liquid volume of up to about 1.5 mL.

20. The method as recited in claim 19, wherein the SC dose is delivered in a liquid volume of about 1 mL to about 1.5 mL.

21. The method as recited in claim 4, wherein the IV, IM, or SC dose or injection contains at least one agent that acts as a non-ionic solubilizer and/or emulsifying agent.

22. The method as recited in claim 2, wherein the symptom(s) of CHS is/are chosen from nausea, vomiting, and/or abdominal pain.

23. The method as recited in claim 2, wherein the onset of treatment, reversal, or reduction of the CHS or one or more symptom(s) thereof is/are apparent within 5-30 minutes following intravenous injection of drinabant, or a salt of polymorph thereof.

24. The method as recited in claim 2, wherein the onset of treatment, reversal, or reduction of the CHS or one or more symptom(s) thereof is/are apparent within 15-45 min following intramuscular administration of drinabant, or a salt or polymorph thereof.

25. The method as recited in claim 2, wherein if no response is observed within about 30 minutes to about two hours of a first administration of drinabant, and the presence of cannabinoids is confirmed or strongly suspected, a second dose may be administered.

26. The method as recited in claim 25, wherein if no response is observed within 30-45 minutes of a first administration of drinabant, and the presence of cannabinoids is confirmed or strongly suspected, a second dose may be administered.

* * * * *